US012758253B2

(12) United States Patent
Bartoli et al.

(10) Patent No.: US 12,758,253 B2
(45) Date of Patent: Oct. 13, 2026

(54) METHOD AND DEVICE FOR PROCESSING IMAGES IN ORDER TO AUTOMATICALLY ESTIMATE THE POSITION OF A TROCAR

(71) Applicants: SURGAR, Clermont-Ferrand (FR); UNIVERSITÉ CLERMONT-AUVERGNE, Clermont-Ferrand (FR); CENTRE NATIONAL DE LA RECHERCHE SCIENTIFIQUE, Paris (FR); CLERMONT AUVERGNE INP, Aubière (FR)

(72) Inventors: Adrien Bartoli, Clermont-Ferrand (FR); Prasad Samarakoon, Romagnat (FR)

(73) Assignees: SURGAR, Clermont-Ferrand (FR); UNIVERSITE CLERMONT AUVERGNE, Clermont-Ferrand (FR); CENTRE NATIONAL DE LA RECHERCHE SCIENTIFIQUE, Paris (FR); CLERMONT AUVERGNE INP., Aubiere (FR)

( * ) Notice: Subject to any disclaimer, the term of this patent is extended or adjusted under 35 U.S.C. 154(b) by 461 days.

(21) Appl. No.: 18/262,915

(22) PCT Filed: Feb. 1, 2022

(86) PCT No.: PCT/EP2022/052367
§ 371 (c)(1),
(2) Date: Jul. 25, 2023

(87) PCT Pub. No.: WO2022/167428
PCT Pub. Date: Aug. 11, 2022

(65) Prior Publication Data

US 2026/0069309 A1 Mar. 12, 2026

(30) Foreign Application Priority Data

Feb. 3, 2021 (FR) ...................................... 2101020

(51) Int. Cl.
*A61B 17/34* (2006.01)
*A61B 1/00* (2006.01)
(Continued)

(52) U.S. Cl.
CPC ...... *A61B 17/3403* (2013.01); *A61B 1/00009* (2013.01); *A61B 1/0005* (2013.01);
(Continued)

(58) Field of Classification Search
CPC ............ A61B 17/3403; A61B 1/00009; A61B 1/3132; G06T 2207/10068; G06T 2207/30021
See application file for complete search history.

(56) References Cited

U.S. PATENT DOCUMENTS 8,391,571 B2 3/2013 Cinquin et al.
10,419,680 B2 * 9/2019 Inoue .................. A61B 1/3132
(Continued)

FOREIGN PATENT DOCUMENTS

CN 102525662 A * 7/2012
JP 2011206312 A * 10/2011 ............. A61B 6/463
(Continued)

OTHER PUBLICATIONS

Lin Dong and G. Morel, "Robust trocar detection and localization during robot-assisted endoscopic surgery," 2016 IEEE International Conference on Robotics and Automation (ICRA), Stockholm, Sweden, 2016, pp. 4109-4114, doi: 10.1109/ICRA.2016.7487602. (Year: 2016).*

(Continued)

*Primary Examiner* — Michael Robert Cammarata
(74) *Attorney, Agent, or Firm* — CRGO Global; Steven M. Greenberg

(57) ABSTRACT

The invention relates to a method for processing images acquired by an endoscope (12), for the automatic estimation
(Continued)

of the position of at least one trocar (58) which is disposed on a wall (56) of the body of a patient, each trocar (58) being configured to permit the passage of an instrument (54) therethrough in order to access a cavity (50) in the body of the patient, characterized in that it comprises a step of acquiring images of the abdominal cavity (50) of the patient using the endoscope (12), each of the images showing at least one instrument (54) passing through each trocar (58), a step of determining, from the images, the position and orientation of the instrument (54) with respect to the position of the endoscope (12), a step of estimating, from the images, the position of each trocar (58) from at least two positions and orientations of the instrument (54).

12 Claims, 4 Drawing Sheets

(51) Int. Cl.
*A61B 1/313* (2006.01)
*G06T 7/73* (2017.01)

(52) U.S. Cl.
CPC .............. *A61B 1/3132* (2013.01); *G06T 7/74* (2017.01); *G06T 2207/10068* (2013.01); *G06T 2207/30021* (2013.01)

(56) References Cited

U.S. PATENT DOCUMENTS

| | | | | |
|---|---|---|---|---|
| 11,304,763 | B2 * | 4/2022 | Shelton, IV | G06T 7/10 |
| 11,612,445 | B2 * | 3/2023 | Shelton, IV | B25J 9/1643 606/130 |
| 12,183,448 | B2 * | 12/2024 | Ichikawa | A61B 90/98 |
| 2007/0265502 | A1 * | 11/2007 | Minosawa | A61B 17/3421 600/173 |
| 2008/0287783 | A1 * | 11/2008 | Anderson | A61B 8/5238 600/429 |
| 2014/0074134 | A1 * | 3/2014 | Skarbnik | A61B 90/90 606/170 |
| 2015/0289755 | A1 * | 10/2015 | Voros | A61B 1/0125 600/109 |
| 2016/0360120 | A1 * | 12/2016 | Inoue | A61B 1/00071 |
| 2018/0225538 | A1 * | 8/2018 | Voros | G06V 20/64 |
| 2019/0201129 | A1 * | 7/2019 | Shelton, IV | G16H 20/40 |
| 2019/0209241 | A1 * | 7/2019 | Begg | A61B 17/3423 |
| 2020/0113636 | A1 * | 4/2020 | Chino | A61B 90/37 |
| 2021/0128243 | A1 * | 5/2021 | Kumar | A61B 90/36 |
| 2021/0330396 | A1 * | 10/2021 | Govari | A61B 1/00158 |
| 2022/0039872 | A1 * | 2/2022 | Leonard | A61B 1/00009 |
| 2024/0000523 | A1 * | 1/2024 | Amat Girbau | A61B 34/30 |

FOREIGN PATENT DOCUMENTS

| | | | | | |
|---|---|---|---|---|---|
| JP | 2018019993 | A | * | 2/2018 | |
| KR | 20180104764 | A | * | 9/2018 | A61B 6/463 |

OTHER PUBLICATIONS

B. Rosa, C. Gruijthuijsen, B. Van Cleynenbreugel, J. Vander Sloten, D. Reynaerts, and E. Vander Poorten, "Estimation of optimal pivot point for remote center of motion alignment in surgery," International journal of computer assisted radiology and surgery, vol. 10, No. 2, pp. 205-215, 2015. (Year: 2015).*

Doignon, Christophe, Pierre Graebling, and Michel De Mathelin. "Real-time segmentation of surgical instruments inside the abdominal cavity using a joint hue saturation color feature." Real-Time Imaging 11.5-6 (2005): 429-442. (Year: 2005).*

Wilson J, Tsao TC, Hubschman J, Schwartz S (2010) Evaluating remote centers of motion for minimally invasive surgical robots by computer vision. In: Advanced Intelligent Mechatronics (AIM), 2010 IEEE/ASME International Conference on, pp. 1413-1418 doi: 10.1109/AIM.2010.5695924 (Year: 2010).*

F. Nageotte, P. Zanne, C. Doignon and M. D. Mathelin, "Visual Servoing-Based Endoscopic Path Following for Robot-Assisted Laparoscopic Surgery," 2006 IEEE/RSJ International Conference on Intelligent Robots and Systems, Beijing, China, 2006, pp. 2364-2369, doi: 10.1109/IROS.2006.282647. (Year: 2006).*

Voros, S., Long, J.-A., and Cinquin, P. (2007). Automatic detection of instruments in laparoscopic images: a first step towards high-level command of robotic endoscopic holders. Int. J. Robot. Res. 26, 1173-1190. doi: 10.1177/027836490708339 (Year: 2007).*

International Search Report received for Application No. PCT/EP2022/052367 mailed Apr. 13, 2022, 3 pages.

* cited by examiner

[Fig. 1]
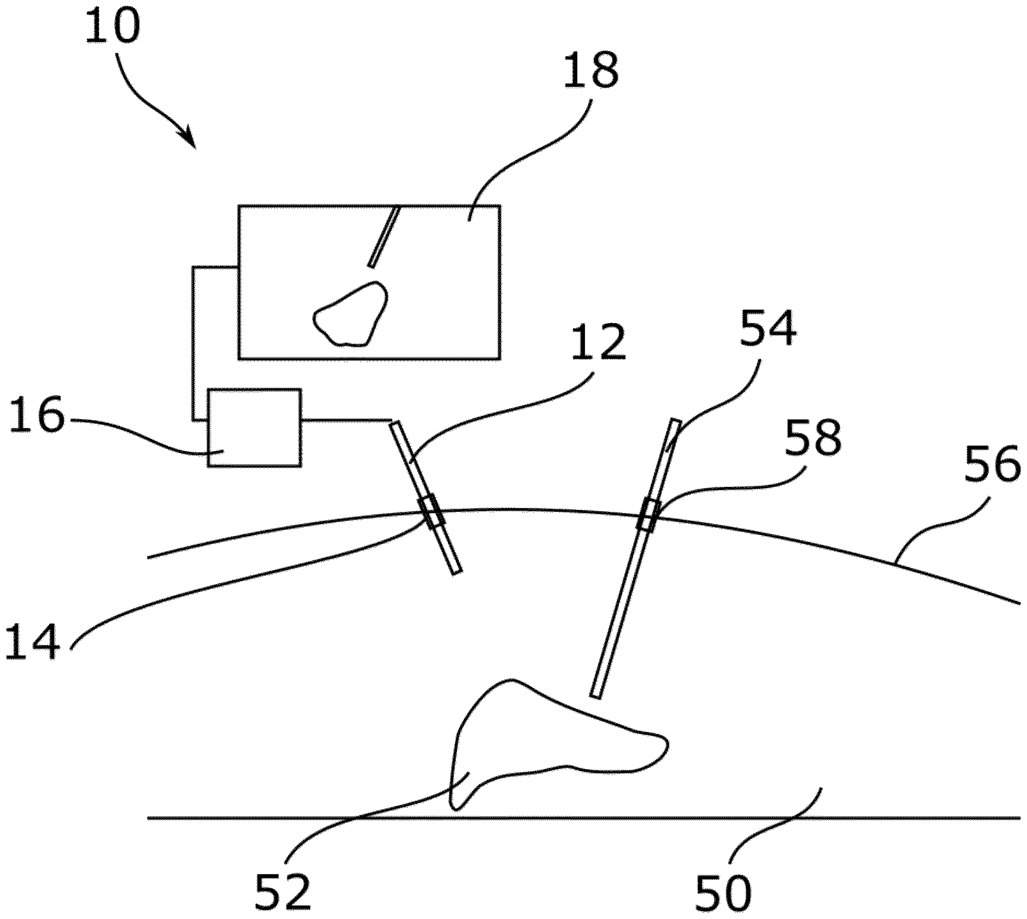

[FIG. 2]
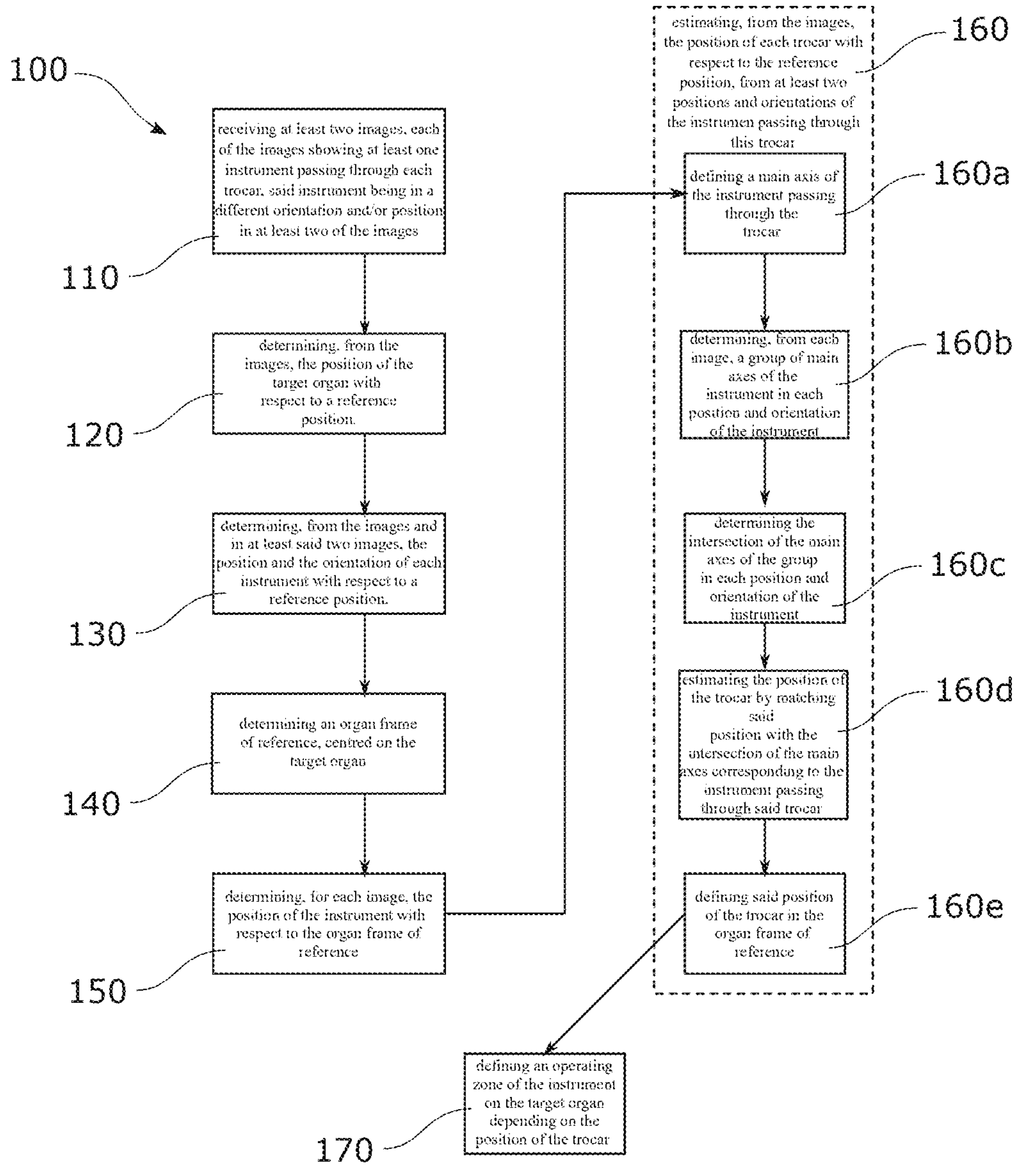

[Fig. 3]
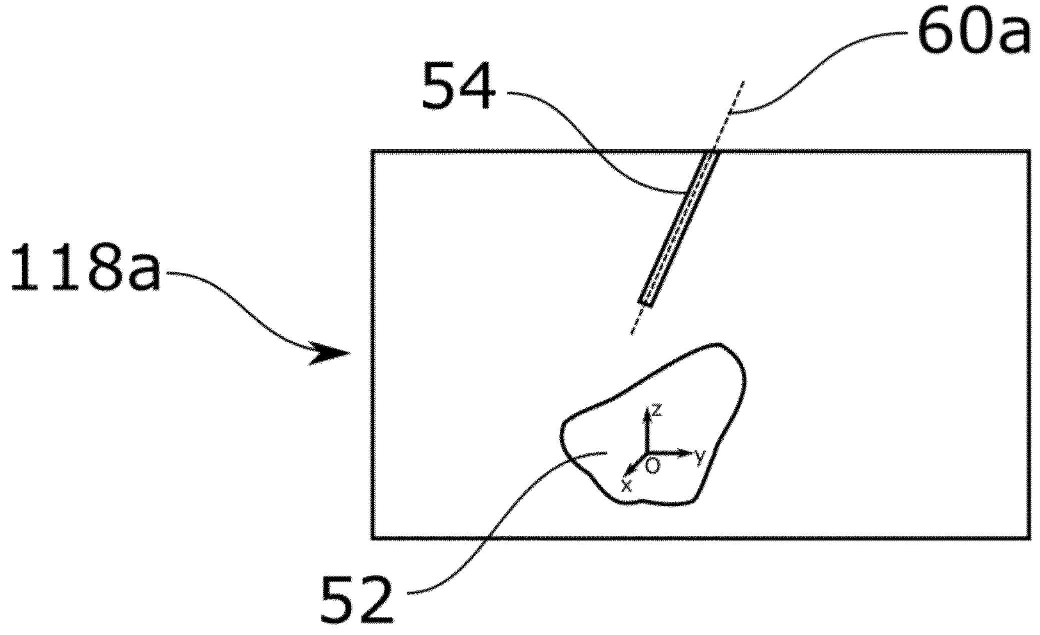
[Fig. 4]
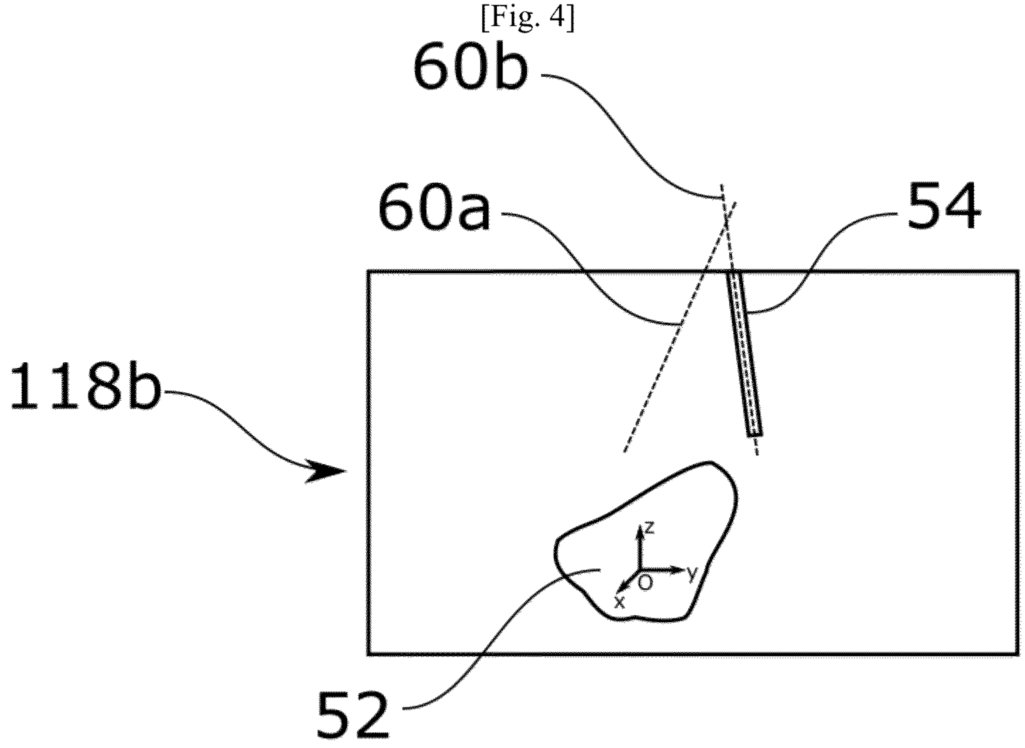

[Fig. 5]
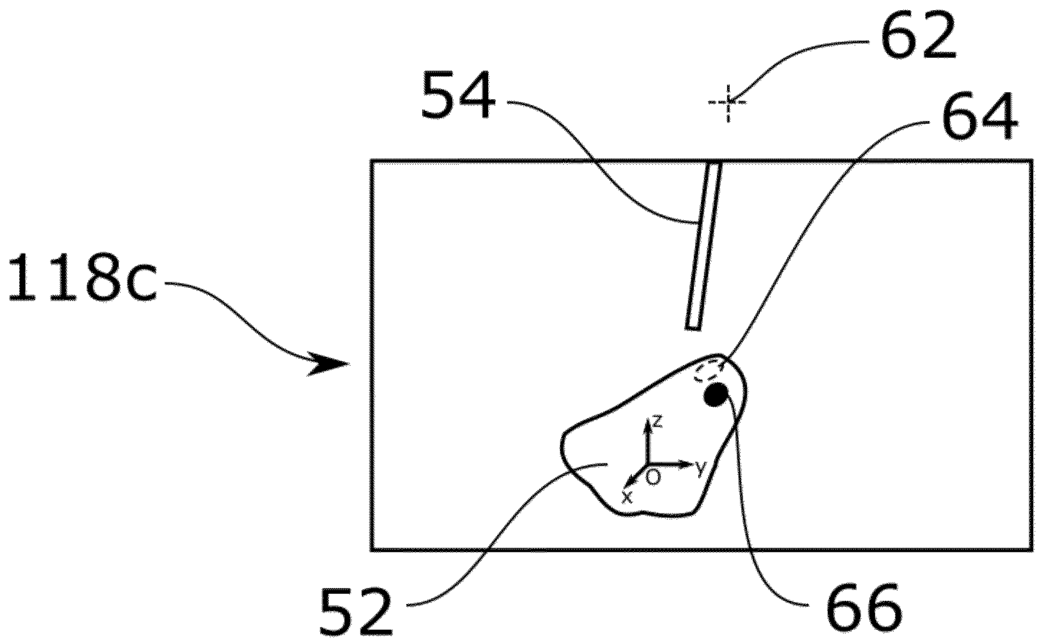

METHOD AND DEVICE FOR PROCESSING IMAGES IN ORDER TO AUTOMATICALLY ESTIMATE THE POSITION OF A TROCAR

TECHNICAL FIELD OF THE INVENTION

The invention relates to a method and a device for processing images for the automatic estimation of the position of a trocar, in particular for the processing of images to assist in endoscopic surgery, in particular laparoscopic surgery. The invention relates more particularly to a method and a device making it possible to estimate in real time the position of a trocar enabling access by an instrument or an endoscope into a cavity in the body of a patient, in particular the abdominal cavity. The invention also relates to an endoscopic imaging system comprising an image-processing device and/or implementing an image-processing method.

TECHNOLOGICAL BACKGROUND

Laparoscopy is a medical technique for visual medical examination of the inside of the body of a patient using an endoscope, or more particularly a laparoscope when it is used to view the abdomen of a patient. An endoscope generally comprises a light source and a means of collecting light, e.g. optical fibers or a video sensor.

During a surgical procedure by laparoscopy, the laparoscope makes it possible to see the abdominal cavity directly or remotely and makes it possible to view the surgical site and to operate directly using surgical instruments. This surgical technique has the advantage of not necessitating a large opening in the abdominal wall (in contrast to laparotomy), making this a minimally invasive technique.

Analogously, minimally invasive surgical procedures using an endoscope can be implemented in the thoracic cavity (thoracoscopy) or in the pelvic cavity. The term endoscopic surgery or surgical endoscopy is generally used.

Recent technological advances have developed laparoscopy from the medical personnel simply viewing the image of the zone to be operated on towards augmented viewing which makes it possible to display on the screen additional information in the viewed image so as to assist medical personnel during the surgery.

In particular, techniques involving viewing by computer are used in the image obtained by the laparoscope in real time in order to provide a complement of information by augmented reality. For example, a hidden structure in the organ, such as a tumor, can be displayed in the image. In particular, it may be desired to display an operating site (e.g. incision) in the image of the organ. More generally, the term computer-guided surgery is used in this respect.

A difficulty in adding the complement of information derives in particular from the transcription of three-dimensional information (the position of the organs, the position of the tumor, the incision site, the position of the blood vessels, etc.) to a two-dimensional image collected by the laparoscope.

In particular, access to the abdomen by the instruments is not unlimited because the instruments pass through portals enabling the wall of the abdomen to be passed through. These portals are called trocars and are generally formed of small tubes placed in an abdominal incision and permitting the passage of the instruments while ensuring the sealing-tightness of the pneumoperitoneum created. A trocar generally permits the passage of a single instrument, and there are generally two or three of these.

These trocars thus limit the placement of the instruments, i.e. the orientations and positions thereof. The addition of information to the image transmitted to the medical personnel must thus take this limitation into account and supply in particular operating information which is compatible with the possible movements and positions of the instruments.

The inventors have thus sought to improve how operating zones of the instrument are determined by virtue of improved determination of the placement of the instrument and the possible movements of the instrument, and in particular the determination of the position of the trocar permitting the instrument to pass through.

AIMS OF THE INVENTION

The invention aims to provide a method and a device for processing images for the automatic estimation of the position of at least one trocar for endoscopic surgery.

The invention aims to provide a method and a device for processing images enabling the limitations of movements and position of the instrument to be better taken into account for the determination of the information assisting the surgical operation.

The invention aims to provide a method and a device for processing images enabling an estimation of the position of each trocar and a real-time adjustment of the estimated position of each trocar as new images are received.

The invention aims to provide a method and a device for processing images, enabling the display of operating zones in an image of an organ on which to operate, depending on the position of the trocar.

DESCRIPTION OF THE INVENTION

In order to do this, the invention relates to a method for processing images for the automatic estimation of the position of at least one trocar, each trocar being configured to permit the passage of a substantially straight instrument therethrough, characterized in that it comprises:

- a step of receiving at least two images, each of the images showing at least one instrument passing through each trocar, said instrument being in a different position and/or orientation in at least two of the images,
- a step of determining, from the images and in at least said two images, the position and the orientation of each instrument with respect to a reference position,
- a step of estimating, from the images, the position of each trocar with respect to the reference position, from at least two positions and orientations of the instrument passing through this trocar.

According to one variant of the invention, the invention relates to a method of processing images for the automatic estimation of the position of at least one trocar disposed on a wall of the body of a patient, each trocar being configured to permit the passage of a substantially straight instrument therethrough in order to access a cavity in the body of the patent beneath the wall, characterized in that it comprises:

- a step of receiving at least two images of the cavity of the patient, each of the images showing at least one instrument passing through each trocar, said instrument being in a different position and/or orientation in at least two of the images,
- a step of determining, from the images and in at least said two images, the position and the orientation of each instrument with respect to a reference position, a step of estimating, from the images, the position of each trocar with respect to the reference position, from at least two positions and orientations of the tool passing through this trocar.

A method of processing images in accordance with the invention thus makes it possible to estimate the position of a trocar, in particular on a wall of the body of a patient automatically and in real time in order to be able to adjust the instructions relating to the movement of the instrument passing through this trocar. A wall of the body of the patient is preferably an abdominal, thoracic or pelvic wall, each trocar preferably permitting access to an abdominal, thoracic and/or pelvic cavity. In this context, the surgical operation is respectively referred to as laparoscopic, thoracic or pelvic surgery, depending on the wall on which the trocar is disposed, irrespective of the cavity accessed.

The method makes it possible to dispense with pre-operative steps of determining the position of the trocar by automatically determining its position. Since the position of the trocar can vary over time, the use of the placement of the instrument passing through the trocar, i.e. its orientation and its position, makes it possible to estimate the position of the trocar permanently. In the two minimum images used to estimate the position of the trocar, it is necessary for the instrument to be in a different position and/or orientation, in particular for there to be, between the two images, a change of position and/or orientation of the instrument which does not leave an axis of the instrument corresponding to its main direction identical. The two images are referred to as e.g. estimation images.

This automatic estimation makes it possible to adapt the information supplied to the medical personnel in real time depending on the estimated position of each trocar. In particular, information in augmented reality displayed on a viewing screen of the endoscope is adjusted depending on the estimated position of the trocar in order to form an augmented endoscopic image, this information taking into account the possible placements of the instrument passing through the trocar depending on the estimated position of the trocar. The estimation of the position of the trocar also makes it possible to resolve certain discrete ambiguities sometimes present in the placement of the instrument, i.e. particular placements of the instrument in which the endoscope information alone is not sufficient to reliably determine the placement of the instrument, but for which an estimation of the position of the trocar makes it possible to provide additional information making it possible to remove the ambiguity as to the placement of the instrument.

In fact, the placements of the instrument are restricted by the position of the trocar which the instrument passes through, and the analysis of at least two of these different placements makes it possible to determine the position of the trocar as a result of its low number of degrees of freedom.

Using the placements of the instruments to determine the position of the trocars, the method also makes it possible to determine the position of a trocar even when this trocar is not visible using the endoscope, since the instrument passing through the trocar is sufficiently visible.

The reference position can be either determined in a frame of reference outside or inside the camera collecting the images, said camera being able to be e.g. an endoscope. An external frame of reference is e.g. a global frame of reference defined in the surgical context, e.g. a frame of reference linked to the organ being viewed or more generally with respect to the environment being viewed, or a frame of reference of a device for positioning the camera (e.g. by optical or electromagnetic tracking). A frame of reference inside the camera or endoscope is e.g. a first position of the camera or of the endoscope at the moment of the acquisition of a first image being defined as a frame of reference for the position of the camera or of the endoscope at the moments of acquisition of the following images, the position of the camera or of the endoscope for the following images being defined relative to this first reference position in the case of inter-image displacement.

Advantageously and in accordance with the invention, the step of estimating the position of each trocar comprises for each trocar:

a sub-step of defining a main axis of the instrument passing through the trocar, a sub-step of determining, from each image, groups of main axes of the instrument in each position and orientation of the instrument, a sub-step of determining the intersection of the main axes of the group in each position and orientation of the instrument, a sub-step of estimating the position of the trocar by matching said position with the intersection of the main axes corresponding to the instrument passing through said trocar.

According to this aspect of the invention, the position of each trocar is determined by the intersection of the axes which the instrument passing through the trocar forms in the at least two images where the instrument is in a different position. Since the movements of the instruments are limited by the access to the cavity in the body of the patient by the trocar, it is possible, from two axes, to determine the position of the trocar because the main axes pass through the trocar. The intersection of the axes can be located outside the zone visible using the endoscope without being detrimental to the estimation of the position of the trocar.

These sub-steps are carried out for each trocar for which it is desired to estimate the position. They can be carried out in parallel for each trocar, e.g. by using the same image for the determination of the main axes of a plurality of instruments which appear on the image, or sequentially, by estimating, one by one, the position of each trocar before carrying out the sub-steps again in order to estimate the position of the following trocar.

Advantageously and according to this last variant of the invention, the determination of the intersections of the main axes of each group of main axes comprises application of a least squares method, or preferably of a robust estimation method such as an M-estimator, to the main axes of the group.

Advantageously and in accordance with the invention, the method comprises a step of determining, from the images, the position of at least one organ visible in at least one of the images, referred to as target organ, with respect to the reference position.

According to this aspect of the invention, the determination of the reference position with respect to the target organ makes it possible to facilitate the determination of the position of each trocar depending on the target organ. Advantageously and in accordance with the invention, this step makes it possible e.g. to determine the position of the target organ with respect to the reference position of the endoscope. The target organ is generally an organ in the cavity in the body of the patient, on which the instrument or instruments will operate during the endoscopic surgical operation necessitating the implementation of the image-processing method.

Advantageously and in accordance with the invention, the method comprises a step of determining an organ frame of reference, centered on the target organ, and a step of determining, for each image, the position of the instrument with respect to the organ frame of reference.

Advantageously and in accordance with the invention, the step of estimating the position of the trocar comprises a sub-step of defining said position of the trocar in the organ frame of reference.

According to this aspect of the invention, the definition of the position of the trocar with respect to the organ frame of reference makes it possible to obtain improved knowledge of the possible operations using the instrument passing through the trocar on the target organ. Furthermore, the definition of the position of the trocar with respect to the target organ, in the frame of reference of the target organ, makes it possible to define the position of the trocar independently with respect to the reference position, e.g. with respect to the position of the endoscope, which makes possible a movement of the endoscope without impacting the definition of the position of the trocar in the organ frame of reference.

Advantageously and in accordance with the invention, the method comprises a step of defining an operating zone of the instrument on the target organ depending on the position of the trocar.

According to this aspect of the invention, the estimation of the position of the trocar makes it possible to determine a possible operating zone of the instrument on the target organ. In fact, the position of the trocar limits the movements of the instrument and the knowledge of this position makes it possible to define and display, e.g. on a viewing screen, the operating zone making it possible to assist the medical personnel to achieve the possibility of effecting the desired operation with the desired instrument.

The invention also relates to a image-processing device, configured for the automatic estimation of the position of at least one trocar, each trocar being configured to permit the passage of a substantially straight instrument therethrough, characterized in that it comprises:

- a receiving unit configured to receive at least two images, each of the images showing at least one instrument passing through each trocar, said instrument being in a different position in at least two of the images,
- a processing unit comprising:
  - a module for determining, from the images, the position and the orientation of the instrument with respect to a reference position,
  - a module for estimating, from the images, the position of each trocar from at least two positions of the instrument passing through this trocar.

A module can e.g. consist of a computing device such as a computer, a group of computing devices, an electronic component or a group of electronic components, or e.g. a computer program, a group of computer programs, a library of a computer program or a computer program function carried out by a computing device such as a computer, a group of computing devices, an electronic component or a group of electronic components.

Advantageously and in accordance with the invention, the image-processing device also comprises an endoscope configured to acquire said at least two images. The receiving unit receives the images acquired by the endoscope.

Advantageously and in accordance with the invention, each trocar is disposed on a wall of the body of a patient during an endoscopy, and the images are images of the abdominal cavity of the patient and each trocar permits the passage of an instrument so as to access the cavity in the body of the patient beneath the wall.

Advantageously and in accordance with the invention, the reference position is a reference position of the endoscope.

Advantageously and in accordance with the invention, the module for estimating the position of each trocar comprises for each trocar:

- a sub-module for defining a main axis of the instrument passing through the trocar,
- a sub-module for determining, from each image, a group of main axes of the instrument in each position and orientation of the instrument,
- a sub-module for determining the intersection of the main axes of the group in each position and orientation of the instrument,
- a sub-module for estimating the position of the trocar by matching said position with the intersection of the main axes corresponding to the instrument passing through said trocar.

Advantageously and in accordance with the invention, the image-processing device comprises a module for determining, from the images, the position of at least one organ visible in at least one of the images, referred to as target organ, with respect to the reference position.

Advantageously and in accordance with the invention, the image-processing device comprises a module for determining an organ frame of reference, centered on the target organ, and a module for determining, for each image, the position of the instrument with respect to the organ frame of reference.

Advantageously and in accordance with the invention, the module for estimating the position of the trocar comprises a sub-module for defining said position of the trocar in the organ frame of reference.

Advantageously and in accordance with the invention, the image-processing device comprises a module for defining an operating zone of the instrument on the target organ depending on the position of the trocar.

Advantageously, the image processing in accordance with the invention is configured to carry out the image-processing method in accordance with the invention.

Advantageously, the image-processing method in accordance with the invention is implemented by an image-processing device in accordance with the invention. In particular, the modules and sub-modules of the device in accordance with the invention are configured to carry out the corresponding steps and sub-steps of the image-processing method in accordance with the invention and the steps and sub-steps of the image-processing method can be carried out by the corresponding modules and sub-modules of the device in accordance with the invention.

The invention also relates to an endoscopic imaging system characterized in that it comprises an image-processing device in accordance with the invention, and a viewing screen, configured to display images received by the image-processing device, in particular in an embodiment with images acquired by the endoscope, and additional information supplied by the processing unit depending on the estimated position of each trocar. The system is preferably used for laparoscopic, thoracoscopic or pelviscopic imaging.

The invention also relates to an image-processing method, an image-processing device and an endoscopic system which are characterized in combination by all or some of the features mentioned above or below.

LIST OF FIGURES

Other aims, features and advantages of the invention will become apparent upon reading the following description given solely in a non-limiting way and which makes reference to the attached figures in which:

FIG. 1 is a schematic view of a laparoscopic imaging system in accordance with one embodiment of the invention, FIG. 2 is a schematic view of the steps of an image-processing method in accordance with one embodiment of the invention, FIG. 3 is a schematic view of a first laparoscopic image obtained by an image-processing method in accordance with one embodiment of the invention, FIG. 4 is a schematic view of a second laparoscopic image obtained by an image-processing method in accordance with one embodiment of the invention, FIG. 5 is a schematic view of an augmented laparoscopic image obtained by an image-processing method in accordance with one embodiment of the invention.

DETAILED DESCRIPTION OF AN EMBODIMENT OF THE INVENTION

In the figures, for the purposes of illustration and clarity, scales and proportions have not been strictly respected.

Furthermore, identical, similar or analogous elements are designated by the same reference signs in all the figures.

FIG. 1 schematically shows a laparoscopic imaging system 10 in accordance with one embodiment of the invention. The object of the system is to make it possible to acquire and diffuse images taken in a cavity 50 in the body of the patient, in this case a cavity in the abdomen of a patient (or abdominal cavity 50), in particular within the scope of laparoscopic surgery. The laparoscopic surgical operation can be intended e.g. for operation on a target organ 52.

In order to do this, the system 10 comprises an image-processing device in accordance with one embodiment of the invention, comprising, in this embodiment, an endoscope 12 configured to acquire images of the abdominal cavity 50 of the patient. The endoscope 12 is disposed in the abdominal cavity 50 of the patient by means of a trocar 14 permitting the endoscope to pass through the abdominal wall. The endoscope used within the area of laparoscopic surgery is currently referred to as a laparoscope. The image-processing device also comprises a receiving unit configured to receive images, in particular the images acquired by the endoscope.

The processing device comprises a plurality of modules making it possible to carry out a method in accordance with the invention, brought together in this case in a processing unit 16. The processing unit 16 is e.g. a computer or electronic board comprising a processor, e.g. a processor dedicated to the processing of images of the method in accordance with the invention or even a general-purpose processor configured to carry out, amongst a number of functions, in particular program instructions for implementation of the steps of the method in accordance with the invention.

The images acquired from the endoscope 12 or the images received by the receiving unit are displayed on a viewing screen 18 intended for the medical personnel. The acquired images can be augmented, i.e. comprise additional information added by the laparoscopic imaging system, which can come from the image-processing device or other devices.

During the laparoscopic surgical operation, the medical personnel are led to operate on the target organ using at least one instrument 54 passing through the abdominal wall 56 by means of a trocar 58. A trocar is e.g. a small tube of synthetic material permitting access to the abdominal cavity while retaining the sealing-tightness of the pneumoperitoneum. The object of the image-processing device is to estimate the position of each trocar 58 permitting passage of instrument 54.

During a conventional laparoscopic surgical operation, between one and three trocars dedicated to the use of instruments in the abdominal cavity may generally be used, in addition to the trocar permitting passage of the endoscope.

An image-processing method 100 according to one embodiment of the invention comprises a number of steps illustrated with reference to FIG. 2.

The image-processing method comprises a step 110 of receiving at least two images, in particular images of the abdominal cavity of the patient, each of the images showing at least one organ of the abdomen, referred to as target organ, and at least one instrument passing through each trocar, said instrument being in a different position in at least two of the images.

The method 100 then comprises a step 120 of determining, from the images, the position of the target organ with respect to a reference position.

The position of the target organ can be determined according to a number of methods. For example, from images acquired by the endoscope or more generally images received during a step of receiving images of the cavity of the patient, it is possible to use a 3D reconstruction solution, or registration of the images acquired with pre-operative data (prior approximate knowledge of the positions of organs likely to be visible in the cavity of the patient, e.g. via the endoscope), or any other solution making it possible to define a fixed 3D frame of reference on the target organ. The 3D reconstruction solution can be effected e.g. by structure-from-motion, or SfM, methods or by simultaneous localization and mapping, or SLAM, methods. For example the 3D reconstruction solution can be implemented by the Meshroom software edited by the ALICEVISION association.

The method 100 then comprises a step 130 of determining, from the images, the position and the orientation of the instrument with respect to the reference position, e.g. the position of the endoscope. Since the position of the instrument is variable, it cannot be determined by pre-operative data. The position of the instrument is thus determined by a 3D reconstruction solution which can be either generic or adapted to the type of instrument used. This latter solution can make it possible to determine the position of the instrument more rapidly and more robustly.

The method 100 then comprises a step 140 of determining an organ frame of reference, centered on the target organ, and a step 150 of determining the reference position with respect to the organ frame of reference. These steps make it possible to better define the positions of each object (trocars, instruments, etc.) in the operational context depending on the target organ which is that on which some of the surgical operations must take place. The definition of the organ frame of reference makes it possible to characterize the relative positions of the different objects independently of the reference position.

The organ frame of reference can be determined according to different methods depending on the target organ. From a 3D object representative of the organ determined in the step of determining the position of the target organ, either by 3D reconstruction or by registration of pre-operative data (in particular a pre-operative 3D model), it is possible to define e.g. the center of mass of this 3D object as the origin and to define main axes of the target organ which will form the 3 axes of the frame of reference of the target organ.

The method 100 then comprises a step 160 of estimating, from the images, the position of each trocar from at least two positions and orientations of the instrument passing through this trocar. This step comprises in particular, in this embodiment of the invention, a plurality of sub-steps.

The step 160 of estimating the position of each trocar comprises a sub-step 160*a* of defining a main axis of each instrument. This step can be carried out in advance and makes it possible to define a main axis for the type of instrument passing through the trocar which it is desired to locate, so as to retain a frame of reference which is constant irrespective of the position of the instrument in the images processed in the following sub-steps. Since the instruments are substantially straight, their main axis is generally defined by the axis on which the instrument extends, characterizing in particular its length.

In practice, the main axis of each instrument passes through the trocar in which the instrument is inserted irrespective of the position of the instrument, and it is by virtue of this property that it will be possible to estimate the position of the trocar.

In order to do this, the step 160 of estimating the position of each trocar comprises a sub-step 160*b* of determining, from each image, groups of main axes of the instruments in each position and orientation of each instrument. This sub-step makes it possible to associate with each instrument a group of main axes representative of the instrument in at least two different orientations and positions.

FIG. 3 schematically shows a first image 118*a* as received for processing by the image-processing method, e.g. acquired by the endoscope, and as can be displayed on the viewing screen 18 described above with reference to FIG. 1. The first image 118*a* shows an instrument 54 and the target organ 52, to which the organ frame of reference Oxyz has been assigned. This first image makes it possible to obtain a first main axis 60*a* associated with the instrument 54 in the position and orientation shown in this first image 118*a*.

FIG. 4 schematically shows a second image 118*b* as received for processing by the image-processing method, e.g. acquired by the endoscope, and as can be displayed on the viewing screen 18 described above with reference to FIG. 1.

The second image 118*b* shows the instrument 54 and the target organ 52 and makes it possible to obtain a second main axis 60*b* associated with the instrument 54 in the position and orientation shown in this image 118*b*.

The first main axis 60*a* and the second main axis 60*b*, both shown in FIG. 4, form a group of main axes associated with the instrument 54.

With reference to FIG. 2, the step 160 of estimating the position of each trocar then comprises a sub-step 160*c* of determining the intersections of the main axes of each group corresponding to a single instrument in each position and orientation of said instrument. The intersection is determined according to a precise statistical criterion, e.g. an intersection in the least squares sense, i.e. by applying the least squares method to the main axes of each group of main axes in order to determine the intersection of said main axes.

As the group of the main axes associated with an instrument pass through the trocar, this intersection makes it possible to estimate the position of the trocar by matching said position with the intersection corresponding to the instrument passing through said trocar. This estimation corresponds to a sub-step 160*d* of estimating the position of each trocar of the step 160 of estimating the position of each trocar.

The step 160 of estimating the position of each trocar finally comprises a sub-step 160*e* of defining said position of the trocar in the organ frame of reference. The position of each trocar is thus expressed according to the organ frame of reference.

FIG. 5 schematically shows an augmented laparoscopic image 118*c* as received for processing by the image-processing method, e.g. acquired by the endoscope, following at least one implementation of the image-processing method described with reference to FIG. 2. The method has made it possible to estimate the position of the trocar 58 visible in FIG. 1 but not visible in the images received by the image-processing method, in particular not visible using the endoscope. According to how the endoscope or the camera able to provide the image processed by the image-processing method is disposed, the trocar could also appear in the image.

Whether or not each trocar is visible, the position thereof is estimated by the intersection 62 of the main axes described above with reference to FIGS. 3 and 4. The estimation of the position of the trocar makes it possible to display additional information such as e.g. an operating zone 64 of the instrument on the target organ depending on the position of the trocar, e.g. in order to operate on a tumor 66 in the target organ 52. This operating zone is determined by a step 170 of defining an operating zone of the instrument on the target organ depending on the position of the trocar of the method 100.

The operating zone is determined depending on the constraints of movement of the instrument, which depend in particular on the shape of the instrument and the position of the trocar.

If the intersection 62 and thus the estimation of the position of the trocar is within the laparoscopic image 118*c*, the estimation of the position of the trocar can also be displayed on the laparoscopic image 118*c* as additional information.

The method is configured to determine in real time the position of the trocar or trocars permitting the passage of the instruments, in the event of modification of the position of the trocar with respect to the target organ (or by movement of the trocar, or by movement of the target organ, or both). The steps of the image-processing method are thus repeated as many times as necessary and the estimation of the position of the trocar adjusted accordingly.

The embodiments shown in FIGS. 1 to 5 are focused on the estimation of the position of a single trocar for reasons of illustration and clarity, but the steps of the image-processing method apply for each trocar for which it is desired to estimate the position and the same steps thus apply for the detection of two or more trocars. The invention is thus not limited to the detection of a single trocar.

The invention is not limited to the embodiment described. In particular, the invention is applicable to any type of endoscopic imaging system within the scope of endoscopy using trocars, e.g. in the thoracic or pelvic cavity. The trocar can be disposed e.g. on a thoracic or pelvic wall. The target organ can be e.g. in the thoracic or pelvic cavity. A trocar and an endoscope which are disposed on an abdominal wall can be used e.g. for an operation on a target organ located in the pelvic or thoracic cavity.

The invention claimed is:

1. An image processing method for processing endoscopic images for the automatic estimation of the position of at least one trocar (58), each trocar (58) being configured to permit the passage of a substantially straight instrument (54) therethrough, characterized in that it comprises:

a step (110) of receiving at least two images (118*a*, 118*b*), each of the images being an endoscopic image showing at least one instrument (54) passing through each trocar (58), said instrument being in a different orientation and/or position in at least two of the images (118*a*, 118*b*), a step (130) of determining, from the images and in at least said two images, the position and the orientation of each instrument (54) with respect to a reference position, a step (160) of estimating, from the images, the position of each trocar (58) with respect to the reference position, from at least two positions and orientations of the instrument (54) passing through this trocar (58), comprising, for each trocar:

a sub-step (160*a*) of defining a main axis (60*a*, 60*b*) of the instrument (54) passing through the trocar (58), a sub-step (160*b*) of determining, from each image, a group of main axes of the instrument in each position and orientation of the instrument, a sub-step (160*c*) of determining the intersection (62) of the main axes of the group in each position and orientation of the instrument, a sub-step (160*d*) of estimating the position of the trocar (58) by matching said position with the intersection (62) of the main axes corresponding to the instrument (54) passing through said trocar (58).

2. Image-processing method as claimed in claim 1, characterized in that it comprises a step (120) of determining, from the images, the position of at least one organ visible in at least one of the images, referred to as target organ (52), with respect to the reference position.

3. Image-processing method as claimed in claim 1, characterized in that it comprises a step (140) of determining an organ frame of reference, centered on the target organ (52), and a step (150) of determining, for each image, the position of the instrument (54) with respect to the organ frame of reference.

4. Image-processing method as claimed in claim 2, characterized in that the step (160) of estimating the position of the trocar (58) comprises a sub-step (160*e*) of defining said position of the trocar (58) in the organ frame of reference.

5. Image-processing method as claimed in claim 1, characterized in that it comprises a step (170) of defining an operating zone (64) of the instrument on the target organ (52) depending on the position of the trocar (58).

6. Image-processing device, configured for the automatic estimation of the position of at least one trocar, each trocar being configured to permit the passage of a substantially straight instrument therethrough, characterized in that it comprises:

a receiving unit configured to receive at least two images, each of the images showing at least one instrument (54) passing through each trocar (58), said instrument (54) being in a different position in at least two of the images, a processing unit (16) comprising:

a module for determining, from the images, the position and the orientation of the instrument (54) with respect to a reference position, a module for estimating, from the images, the position of each trocar (58) from at least two positions of the instrument (54) passing through this trocar (58).

7. Image-processing device as claimed in claim 6, characterized in that the module for estimating the position of each trocar (58) comprises for each trocar:

a sub-module for defining a main axis (60*a*, 60*b*) of the instrument (54) passing through the trocar (58), a sub-module for determining, from each image, a group of main axes of the instrument in each position and orientation of the instrument, a sub-module for determining the intersection (62) of the main axes of the group in each position and orientation of the instrument, a sub-module for estimating the position of the trocar (58) by matching said position with the intersection (62) of the main axes corresponding to the instrument (54) passing through said trocar (58).

8. Image-processing device as claimed in claim 6, characterized in that it comprises a module (120) for determining, from the images, the position of at least one organ visible in at least one of the images, referred to as target organ (52), with respect to the reference position.

9. Image-processing device as claimed in claim 8, characterized in that it comprises a module for determining an organ frame of reference, centered on the target organ (52), and a module for determining, for each image, the position of the instrument (54) with respect to the organ frame of reference.

10. Image-processing device as claimed in claim 9, characterized in that the module for estimating the position of the trocar (58) comprises a sub-module for defining said position of the trocar (58) in the organ frame of reference.

11. Image-processing device as claimed in claim 8, characterized in that it comprises a module for defining an operating zone (64) of the instrument on the target organ (52) depending on the position of the trocar (58).

12. Endoscopic imaging system, characterized in that it comprises an image-processing device as claimed in claim 6 and a viewing screen (18) which is configured to display images received by the image-processing device and additional information supplied by the processing unit (16) depending on the estimated position of each trocar (58).

* * * * *